(12) United States Patent
Aoyagi et al.

(10) Patent No.: US 11,458,977 B2
(45) Date of Patent: Oct. 4, 2022

(54) DRIVING LOAD ESTIMATION APPARATUS

(71) Applicants: Marelli Corporation, Saitama (JP); Shibaura Institute of Technology, Tokyo (JP)

(72) Inventors: Soichiro Aoyagi, Saitama (JP); Haruhiko Satou, Saitama (JP); Toshio Ito, Saitama (JP)

(73) Assignees: Marelli Corporation, Saitama (JP); Shibaura Institute of Technology, Tokyo (JP)

( * ) Notice: Subject to any disclaimer, the term of this patent is extended or adjusted under 35 U.S.C. 154(b) by 305 days.

(21) Appl. No.: 16/616,135

(22) PCT Filed: Apr. 13, 2018

(86) PCT No.: PCT/JP2018/015620
§ 371 (c)(1),
(2) Date: Nov. 22, 2019

(87) PCT Pub. No.: WO2018/216394
PCT Pub. Date: Nov. 29, 2018

(65) Prior Publication Data
US 2020/0079384 A1 Mar. 12, 2020

(30) Foreign Application Priority Data
May 23, 2017 (JP) .............................. JP2017-102101

(51) Int. Cl.
*B60W 40/08* (2012.01)
*A61B 5/18* (2006.01)
(Continued)

(52) U.S. Cl.
CPC .............. *B60W 40/08* (2013.01); *A61B 5/18* (2013.01); *B60W 50/08* (2013.01); *G06F 3/013* (2013.01);
(Continued)

(58) Field of Classification Search
CPC ............. B60W 40/08; B60W 2540/00; B60W 2540/18; B60W 2554/20; B60W 2554/40;
(Continued)

(56) References Cited

U.S. PATENT DOCUMENTS

| | | | |
|---|---|---|---|
| 2015/0169834 A1* | 6/2015 | Nishimura | ............. G16H 50/20 |
| | | | 702/19 |
| 2015/0307105 A1* | 10/2015 | Huber | ................... B60W 40/08 |
| | | | 340/576 |

(Continued)

FOREIGN PATENT DOCUMENTS

| | | | |
|---|---|---|---|
| JP | 2006-138994 A | | 6/2006 |
| JP | 2006138994 A | * | 6/2006 |
| JP | 2016-62359 A | | 4/2016 |

OTHER PUBLICATIONS

Entry on "chunking" from the APA Dictionary of Psychology, accessed at dictionary.apa.org/chunking (Year: 2021).*

(Continued)

*Primary Examiner* — Peter D Nolan
*Assistant Examiner* — Tanya C Sienko
(74) *Attorney, Agent, or Firm* — Young Basile Hanlon & MacFarlane, P.C.

(57) ABSTRACT

A driving load estimation apparatus can estimate the driving load of individual drivers in accordance with the driving environment. The driving load estimation apparatus can include a first VACP calculator configured to calculate a first VACP value based on information related to a driving environment of a vehicle and a correction value calculator configured to calculate a VACP correction value of each driver based on a steering operation in the driving environment. The driving load estimation apparatus estimates a driving load of the driver by correcting the first VACP value based on the VACP correction value.

8 Claims, 5 Drawing Sheets

(51) Int. Cl.
*B60W 50/08* (2020.01)
*G06F 3/01* (2006.01)
*G06F 3/04817* (2022.01)
*B60W 50/00* (2006.01)

(52) U.S. Cl.
CPC . *G06F 3/04817* (2013.01); *B60W 2050/0088* (2013.01); *B60W 2400/00* (2013.01); *B60W 2540/22* (2013.01)

(58) Field of Classification Search
CPC ....... B60W 2554/406; B60W 2554/80; B60W 40/09; B60W 50/08; B60W 2050/0088; B60W 2400/00; B60W 2540/22; A61B 5/18; A61B 5/1128; A61B 5/163; G08G 1/00; G06F 3/013; G06F 3/04817
See application file for complete search history.

(56) References Cited

U.S. PATENT DOCUMENTS

| | | | | |
|---|---|---|---|---|
| 2017/0017851 | A1* | 1/2017 | Matsui | G06V 20/597 |
| 2017/0261609 | A1 | 9/2017 | Tsunoda et al. | |
| 2018/0204572 | A1* | 7/2018 | Manabe | G10L 13/00 |
| 2018/0268695 | A1* | 9/2018 | Agnew | B60K 28/066 |
| 2018/0297611 | A1* | 10/2018 | Fujisawa | B60W 50/14 |
| 2018/0362053 | A1* | 12/2018 | Isa | B60R 1/00 |
| 2019/0001994 | A1* | 1/2019 | Isaji | B62D 15/025 |
| 2019/0049261 | A1* | 2/2019 | Colby | G01C 21/3641 |

OTHER PUBLICATIONS

"Minimize Cognitive Load to Maximize Useability" by K.Whitenton, from NN/g Nieldsen Norman Group, downloaded from https://www.nngroup.com/articles/minimize-cognitive-load/ (Year: 2013).*

"An Integrated Approach to Subjective Measuring Commercial Aviation Pilot Workload" by Y.Zhang et al; .2015 IEEE 10th Conference of Industrial Electronics and Applications (ICIEA) pp. 1093-1098. (Year: 2015).*

International Preliminary Report on Patentability dated Nov. 26, 2019 from International Application No. PCT/JP2018/015620.

Uchida et al., A Study of Driver Workload Estimation by the VACP Method, Transactions of Society of Automotive Engineers of Japan, vol. 46, No. 6, pp. 1171-1176 (2015); 9 pages with partial English Translation.

* cited by examiner

| Chunk count | VACP | Display content | Chunk count | VACP | Display content |
|---|---|---|---|---|---|
| 3 | 4.7 | Today's physical condition / Good | 10 | 15.7 | Notice of appointment for physical exam / Friday, December XX, 13:00 / Minato *** Center |
| 6 | 9.4 | *** three towers★ (map) | 11 | 17.2 | Recommended restaurants nearby / JA *** *** restaurant / *** Japanese restaurant Local sake and sashimi bowl |
| 6 | 9.4 | *** station was *** station when railway opened | 15 | 23.5 | Today's physical condition / Weight: 72 kg (70) / Blood pressure: 116/63 (115/70) / Pulse: 73 (72) / Good / Numbers in parentheses are standard values |
| 7 | 11 | ***lock 21 / Only 4 out of the 60 gondolas are transparent | 17 | 26.6 | XX/XX/20XX / 9:00 Business communication / 10:00 Management meeting / 12:00 Lunch / 13:00 Financial results briefing / 15:00 Meet with President *** of *** Bank / Lunch after meeting / 18:00 |
| 8 | 12.5 | Calorie management / Standard: 1800 kcal / Intake: 550 kcal / Today's predicted intake: 1700 kcal | 17 | 26.6 | Notice of appointment for physical exam / Friday, December XX, 13:00 / Minato *** Center / Last year, the liver... |
| 9 | 14.1 | *** three towers★ / Named by *** on foreign ship / ee Ja**★ ★Ki** | 23 | 36 | XX/XX/20XX / 9:00 Business communication At your seat / 10:00 Management meeting Conference room 90 / 12:00 Lunch / 13:00 Financial results briefing / Hall / 15:00 Meet with President *** of *** Bank / Lunch after meeting Conference room 91 / 18:00 ***gawa Japanese cuisine |
| 10 | 15.7 | Recommended restaurants nearby / *** Japanese restaurant Local sake and sashimi bowl / JA *** *** restaurant | | | |

US 11,458,977 B2

DRIVING LOAD ESTIMATION APPARATUS

CROSS-REFERENCE TO RELATED APPLICATION(S)

The present application is a 371 application of International Application Serial No. PCT/JP2018/015620, filed on Apr. 13, 2018, which claims priority to and the benefit of Japanese Patent Application No. 2017-102101 filed May 23, 2017, the entire contents of which are incorporated herein by reference.

TECHNICAL FIELD

The present disclosure relates to a driving load estimation apparatus mounted in a vehicle.

BACKGROUND

A method is known for uniformly scoring the driving actions of a driver, who drives a vehicle, based on information of the driving environment.

An index called VACP is used at the design stage of aircraft to quantitatively estimate the cognitive resources necessary for various operations in order to estimate the workload of a pilot. The driver workload estimation method disclosed in "A Study of Driver Workload Estimation by the VACP Method", Transactions of Society of Automotive Engineers of Japan, Vol. 46, No. 6, pp. 1171-1176 (2015) (hereinafter "NPL 1"), applies VACP to the driving actions of a driver who is driving a vehicle.

SUMMARY

The aforementioned method that applies VACP, however, uniformly scores the driving actions of the driver based on information of the driving environment and therefore does not take into consideration the differences in driving load between drivers.

The present disclosure was conceived in light of the above problem and aims to provide a driving load estimation apparatus that can estimate the driving load of individual drivers in accordance with the driving environment.

To resolve the above problem, a driving load estimation apparatus according to an embodiment of the present disclosure includes:

a first VACP calculator configured to calculate a first VACP value based on information related to a driving environment of a vehicle;

a steering entropy calculator configured to calculate a steering entropy value of a driver based on information related to a steering angle; and a correction value calculator configured to calculate a VACP correction value of the driver based on the steering entropy value of the driver;

wherein the driving load estimation apparatus is configured to estimate a driving load of the driver by correcting the first VACP value based on the VACP correction value; and wherein the correction value calculator is configured to:
 calculate an individual VACP value, based on the steering entropy value of the driver, as a VACP value of the driver for a steering operation in the driving environment;
 calculate a general VACP value, based on the steering entropy value of the driver and a general relational expression indicating a relationship between the steering entropy value and a VACP value of a general driver, as a VACP value of a general driver for a steering operation in the driving environment; and acquire the VACP correction value based on the general VACP value and the individual VACP value.

A driving load estimation apparatus according to an embodiment of the present disclosure can estimate the driving load of individual drivers in accordance with the driving environment.

DETAILED DESCRIPTION

Embodiments of the present disclosure are described below with reference to the drawings.

Figure 1:
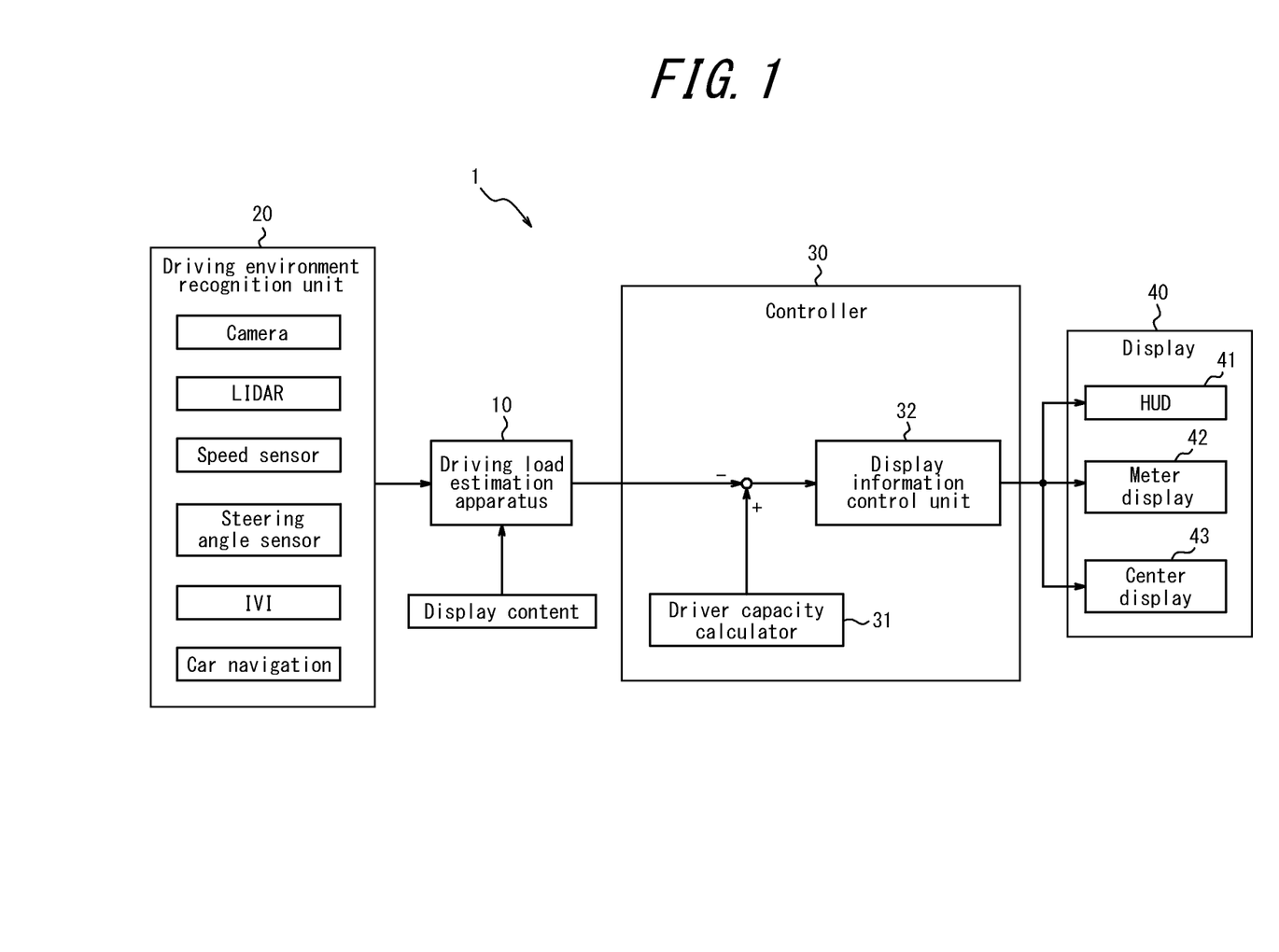
FIG. 1 is a block diagram illustrating an information control system that includes a driving load estimation apparatus according to an embodiment.

FIG. 1 is a block diagram illustrating an information control system 1 that includes a driving load estimation apparatus 10 according to an embodiment. The driving load estimation apparatus 10 according to an embodiment forms part of an information control system 1 of a vehicle.

In addition to the driving load estimation apparatus 10, the information control system 1 includes a driving environment recognition unit 20, a controller 30, and a display 40 as the main constituent elements. The information control system 1 controls display information displayed on the display 40 on the basis of the driving load of each driver estimated in real time by the driving load estimation apparatus 10. For example, the information control system 1 changes at least one of the display position and information amount of the display information based on the driving load of each driver.

The driving environment recognition unit 20 acquires information related to a driving environment of the vehicle. The information related to the driving environment of the vehicle includes environment information around the vehicle and information related to the current position of the vehicle, as described below.

The driving environment recognition unit 20 is configured by suitable sensors such as a camera, light detection and ranging (LiDAR), a speed sensor, and a steering angle sensor. The driving environment recognition unit 20 may include an appropriate sensor configuring an in-vehicle infotainment (IVI) system. The driving environment recognition unit 20 detects traffic participant conditions, such as the characteristics, positions, and movement speed of traffic participants; road conditions, such as the state of the road surface, the distance between lane markings on the road, the type of road, and the number of lanes; traffic light conditions; and the like to acquire environment information around the vehicle. The driving environment recognition unit 20 may acquire information related to at least one of the conditions of vehicles ahead, conditions of vehicles behind, conditions of vehicles in parallel, and conditions of intersecting vehicles. Additionally, the driving environment recognition unit 20 may acquire environment information around the vehicle such as information related to the state of communication with an external network, information related to conditions of moving objects in the surrounding sky, external server information, and point of interest (POI) information.

The driving environment recognition unit 20 may include a navigation system. In this case, the driving environment recognition unit 20 calculates the current position of the vehicle indicated by the latitude, longitude, altitude, inclination, lane position, and the like of the vehicle. The driving environment recognition unit 20 may acquire information related to vehicle position conditions, such as the temperature, humidity, weather, brightness, degree of transparency, and the like at the current position of the vehicle.

The driving environment recognition unit 20 may also acquire various other information related to the driving environment of the vehicle. The driving environment recognition unit 20 may, for example, acquire various information related to vehicle conditions using a controller area network (CAN), which is one communication method in an in-vehicle network. For example, the driving environment recognition unit 20 may acquire information related to vehicle conditions such as the vehicle speed, accelerator state, brake state, clutch state, turn signal state, gear state, windshield wiper state, side mirror state, seat state, audio state, warning state, light state, steering state, idle state, air conditioner state, seat belt state, and driving operation level.

The driving environment recognition unit 20 also acquires information related to the driver. For example, the driving environment recognition unit 20 may acquire information related to the state of the driver. The driving environment recognition unit 20 may, for example, acquire information related to the state of the driver such as the face orientation, gaze, and blinking state of the driver.

The aforementioned information acquired by the driving environment recognition unit 20 is outputted to the driving load estimation apparatus 10.

The controller 30 is a processor that controls and manages the entire information control system 1, including the functional blocks of the information control system 1. The controller 30 is a processor such as a central processing unit (CPU) that executes a program with prescribed control procedures. Such programs are stored in any suitable storage medium.

The controller 30 includes a driver capacity calculator 31 and a display information control unit 32. The controller 30 compares the driving load of each driver as estimated by the driving load estimation apparatus 10 with the capacity of the driver for the driving load as calculated by the driver capacity calculator 31.

For example, when the driver is poor at performing tasks in parallel other than driving, such as looking at the display 40 or operating the air conditioner while driving, the capacity of the driver for the driving load reduces. When the capacity of the driver for the driving load is low, the controller 30 provides display information to the user with a certain limit on the information amount, for example, even if the driving load of each driver estimated by the driving load estimation apparatus 10 is low. In this way, the controller 30 also acquires the capacity of the driver for the driving load with the driver capacity calculator 31, in addition to the driving load of each driver as estimated by the driving load estimation apparatus 10, to control display information more appropriately.

The display information control unit 32 controls display information to output to the display 40 based on the driving load of each driver and the capacity of the driver for the driving load. For example, the display information control unit 32 controls at least one of the display position and the information amount of the display information in accordance with the driving load of each driver and the capacity of the driver for the driving load. The display information control unit 32 outputs the controlled display information to the display 40.

There are various types of display information, i.e. display content. For example, the display content is broadly classified into vehicle information, surrounding information, vehicle outside information, internally recorded information, and information from a communication terminal. The vehicle information includes information related to the vehicle speed, fuel level, and tire air pressure, for example. The surrounding information includes environment information around the vehicle sensed by the sensors configuring the driving environment recognition unit 20. For example, the surrounding information includes information related to the speed limit and other signs. The vehicle outside information includes information on the outside of the vehicle, other than the surrounding information. For example, the vehicle outside information includes external open information, such as map information, infrastructure information, traffic information, and POI information. The internally recorded information includes local information, stored in a storage medium or the like, that does not correspond to any of the vehicle information, surrounding information, and vehicle outside information. The information from a communication terminal includes information, and a history thereof, acquired via an in-vehicle or personal communication terminal. For example, the information from a communication terminal includes information such as an emergency disaster bulletin, an extra edition, e-mail, a social networking service (SNS) message, news, and weather.

The display 40 displays the display information outputted from the display information control unit 32. The display 40 displays various types of display content. The display 40 includes at least one screen. The display 40 may be configured by any display apparatus, such as a liquid crystal display. The display 40 is disposed in the instrument panel, for example, when configured by a liquid crystal display. The display apparatus configuring the display 40 may be a touch panel display or a display incapable of touch operations.

The display 40 is, for example, configured by three screens. The display 40 is configured by a head-up display (HUD) 41, a meter display 42, and a center display 43. The HUD apparatus that includes the HUD 41 has a light emitter that emits display information as display light. The HUD apparatus reflects the generated display light towards an observer, such as a driver, to display a virtual image beyond the front windshield. The observer is not limited to the driver and may, for example, be a passenger seated in the passenger seat. The meter display 42 and the center display 43 are disposed in the instrument panel.

Figure 2:
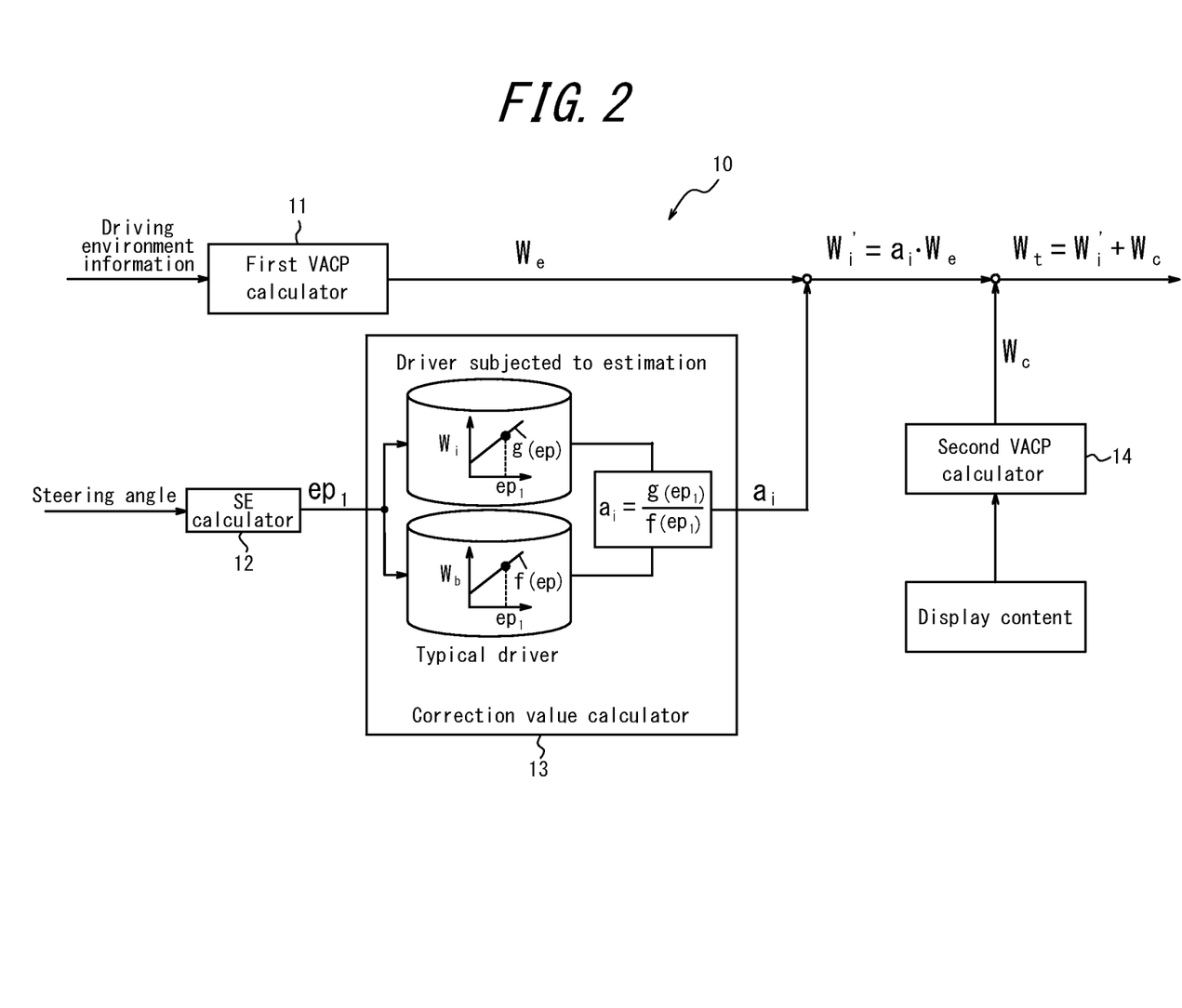
FIG. 2 is a block diagram illustrating the configuration of the driving load estimation apparatus according to an embodiment.

FIG. 2 is a block diagram illustrating the configuration of the driving load estimation apparatus 10 according to an embodiment. The driving load estimation apparatus 10 includes a first VACP calculator 11, a steering entropy (SE) calculator 12, a correction value calculator 13, and a second VACP calculator 14. The driving load estimation apparatus 10 estimates the driving load of a driver from the driving environment in real time by correcting the VACP value, calculated by the first VACP calculator 11, based on the VACP correction value calculated by the correction value calculator 13.

The first VACP calculator 11 calculates a VACP value (first VACP value $W_e$), applied to the driving actions of the driver who is driving the vehicle, based on the information related to the driving environment of the vehicle as acquired by the driving environment recognition unit 20. A conventional VACP value for estimating the workload of a pilot is concretely illustrated in Table 1 below.

TABLE 1

| Scale | Definition |
|---|---|
| Visual (V) | |
| 1.0 | Visually register/detect image |
| 3.7 | Visually discriminate |
| 4.0 | Visually inspect/check |
| 5.0 | Visually locate/align |
| 5.4 | Visually track/follow |
| 5.9 | Visually read (symbol) |
| 7.0 | Visually scan/search/monitor |
| Auditory (A) | |
| 1.0 | Detect/register sound |
| 2.0 | Orient to sound (general) |
| 4.2 | Orient to sound (selective) |
| 4.3 | Verify auditory feedback |
| 4.9 | Interpret semantic content (speech) |
| 6.6 | Discriminate sound characteristics |
| 7.0 | Interpret sound patterns |
| Cognitive (C) | |
| 1.0 | Automatic (simple association) |
| 1.2 | Alternative selection |
| 3.7 | Sign/signal recognition |
| 4.6 | Evaluation/judgment (consider single aspect) |
| 5.3 | Encoding/decoding, recall |
| 6.8 | Evaluation/judgment (consider several aspects) |
| 7.0 | Estimation, calculation, conversion |
| Psychomotor (P) | |
| 1.0 | Speech |
| 2.2 | Discrete actuation (button, toggle, trigger) |
| 2.6 | Continuous adjustive |
| 4.6 | Manipulative |
| 5.8 | Discrete adjustment |
| 6.5 | Symbolic production (writing) |
| 7.0 | Serial discrete manipulation (keyboard entries) |

VACP is a method for dividing human actions into four elements, i.e. visual (V), auditory (A), cognitive (C), and psychomotor (P), and representing the actions numerically from 1.0 to 7.0 in accordance with the amount of cognitive resources consumed. The sum of the numerical values of the four elements indicates the load. The amount of cognitive resources consumed is defined by research using the paired comparison method. On this basis, the VACP value related to vehicle driving operations is estimated, as disclosed in NPL 1. The information control system 1 can judge the driving load of each driver objectively when the driving load estimation apparatus 10 estimates the VACP value of the driving actions for each driver. The information control system 1 judges that the driving load of the driver is small when the VACP is low and that the driving load of the driver is large when the VACP is high.

The first VACP calculator 11 uniformly calculates the first VACP value $W_e$ by associating the driving actions of a driver typically determined from the driving environment of a vehicle with the estimated VACP value related to the driving operations of the vehicle. The first VACP value $W_e$ does not indicate the driving load for each driver but rather is a value calculated uniformly only from information related to the driving environment of the vehicle, as acquired by the driving environment recognition unit 20, with no dependence on individual drivers. Drivers may vary, however, from beginners with little driving experience to veterans with much driving experience. When individual drivers have different degrees of experience in this way, the information control system 1 cannot perform appropriate display control by merely estimating the driving load of the driver uniformly using the first VACP value $W_e$. The SE calculator 12 and the correction value calculator 13 of the driving load estimation apparatus 10, which are provided for appropriately estimating the driving load of each driver, are described below in detail.

The SE calculator 12 calculates the SE value of the driver based on information related to a steering operation acquired by the driving environment recognition unit 20. In greater detail, the SE calculator 12 calculates the SE value of the driver based on information related to the steering angle. Typically, the driver predicts information ahead and unconsciously performs a steering operation smoothly. When the driver performs tasks other than driving, however, the driver's attention and gaze are diverted from the act of driving. The driver can therefore no longer perform a steering operation smoothly. The SE value is a quantification, as an information entropy value calculated from time series steering angle data, of the smoothness of a steering operation by the driver in correspondence with such a tendency by the driver. When the driver is performing a smooth steering operation as usual, the SE decreases. On the other hand, the SE increases when the driver performs an unsmooth steering operation accompanied by a sudden change.

The correction value calculator 13 calculates the VACP correction value of each driver. In greater detail, the correction value calculator 13 derives a general relational expression $f(ep_g)$ between a VACP value $W_b$ and an SE value ep of a general driver based on correlation data between the SE value and VACP value of a general driver (see Expression 1).

$$W_b = f(ep) \qquad \text{(Expression 1)}$$

The VACP of the driver can be calculated by adding up the VACP values determined for the driving actions based on the information related to the state of the driver such as the face orientation, gaze, and blinking state of the driver, for example acquired by the camera or the like during driving, and the environment information around the vehicle. The SE value of the driver can be calculated based on the information related to the steering state, for example acquired by the steering angle sensor during driving.

The correlation data between the SE value of a general driver and the VACP value of a general driver is calculated statistically in advance from the SE value and VACP value, associated and calculated by a method such as the one above, of a plurality of drivers. In this case, the VACP value $W_b$ of a general driver may, for example, be the average VACP value of a plurality of drivers. The correlation data between the SE value and the VACP of a general driver may be stored in any suitable storage medium as a database.

The correction value calculator 13 derives an individual relational expression $g(ep)$ between a VACP value $W_i$, and an SE value $ep_i$ of an individual based on correlation data between the SE value $ep_i$ and the VACP value $W_i$ (see Expression 2).

$$W_i = g(ep) \qquad \text{(Expression 2)}$$

The correlation data between the SE value and the VACP value of each driver can be acquired by storing, in a database, the SE value and the VACP value associated and calculated by a method such as the one above. The correlation data between the SE value and the VACP of each driver may be stored in any suitable storage medium.

Based on the general relational expression $f(ep_g)$ and the individual relational expression $g(ep)$, the correction value calculator 13 calculates a general VACP value $f(ep_1)$ and an individual VACP value $g(ep_1)$ corresponding to an SE value $ep_1$ calculated by the SE calculator 12. The correction value calculator 13 acquires a VACP correction value $a_i$, by calculating the ratio of the individual VACP value $g(ep_1)$ to the general VACP value $f(ep_1)$ (see Expression 3).

$$a_i = \frac{g(ep_1)}{f(ep_1)} \quad \text{(Expression 3)}$$

The driving load estimation apparatus 10 corrects the first VACP value $W_e$ by multiplying the first VACP value $W_e$ by the VACP correction value $a_i$ calculated by the correction value calculator 13. The corrected first VACP value $W_e$ is represented below as $W_i'$ (see Expression 4).

$$W_i' = a_i \cdot W_e \quad \text{(Expression 4)}$$

In this way, the driving load estimation apparatus 10 can represent the driving load of a driver using a VACP value corrected for individual differences. On the other hand, the information control system 1 also defines the load in accordance with the information amount of the display content displayed on the display 40 and compares the load with the aforementioned driving load of an individual driver based on driving actions. From this perspective, the driving load estimation apparatus 10 may include a second VACP calculator 14 in addition to the first VACP calculator 11.

The second VACP calculator 14 calculates a VACP value (second VACP value $W_c$) based on the information amount of the display content displayed on the display 40. The second VACP calculator 14 calculates the second VACP value $W_c$ in correspondence with the information amount of the display content.

For example, the information amount of the display content may be determined by a chunk count defined by a character count, a word count, a count of phrases, icons, and figures, or a count of attention points in graphic form. A "chunk" is a unit of short-term memory. In greater detail, a "chunk" is a unit indicating the information amount when a number of letters are re-encoded as one word and considered to be one block. For example, the chunk count of various signs is calculated taking each place name on an information sign as one chunk, a whole direction as one chunk, and one type of regulatory sign as one chunk. For the information display on an electric bulletin board, the chunk count is calculated taking one part of speech in a sentence as a chunk, without counting auxiliary verbs, particles, and conjunctions as chunks.

The second VACP calculator 14 calculates the chunk count of the display content using such an approach. For the calculated chunk count, the second VACP calculator 14 calculates the VACP value (second VACP value $W_c$) of the display content based on the VACP scale in Table 1.

The driving load estimation apparatus 10 estimates a total driving load $W_t$ by adding the second VACP value $W_c$ to the corrected first VACP value $W_i'$ (see Expression (5)).

$$W_t = W_i' + W_c \quad \text{(Expression 5)}$$

Figure 3:
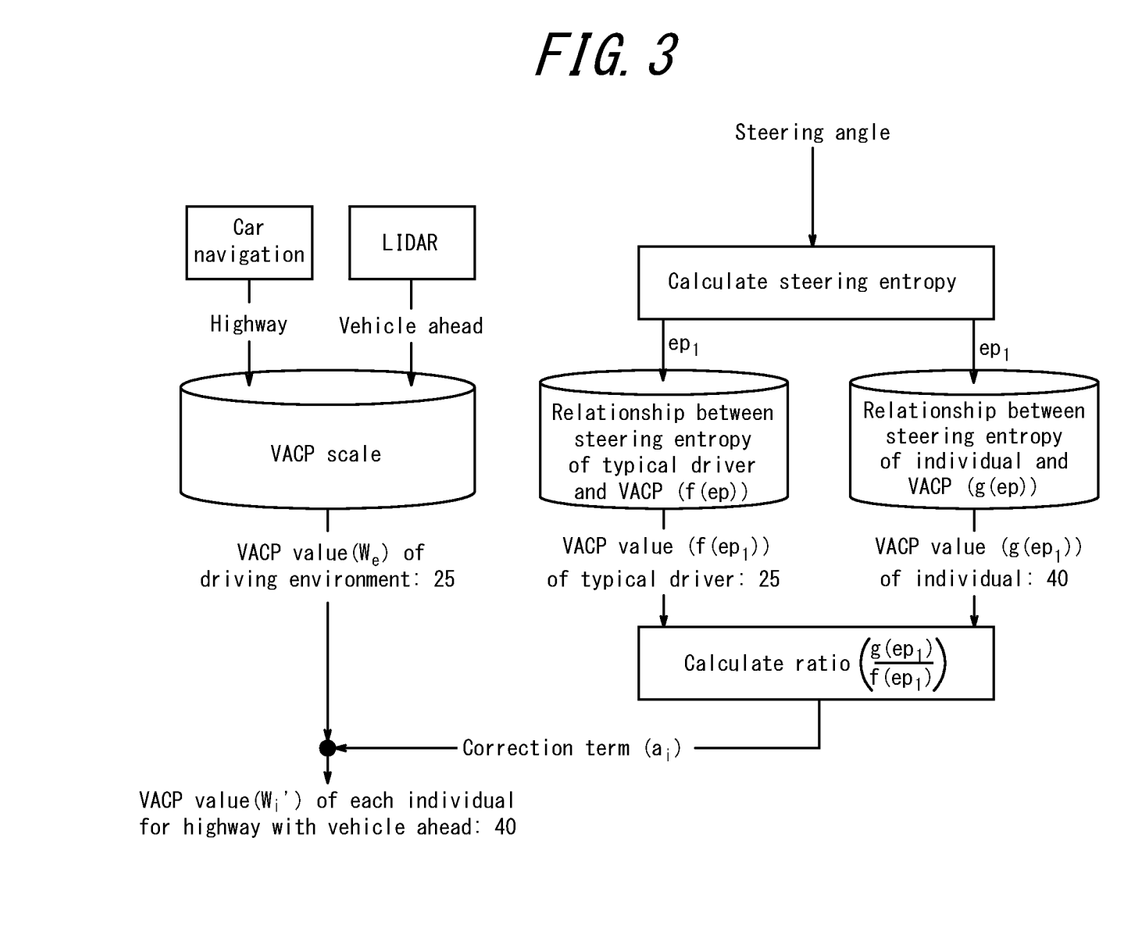
FIG. 3 illustrates an example of correction of a first VACP value by a correction value calculator.

FIG. 3 illustrates an example of correction of the first VACP value $W_e$ by the correction value calculator 13.

The first VACP calculator 11 uses the navigation system and LIDAR forming the driving environment recognition unit 20 to acquire information related to the driving environment of the vehicle, for example that the vehicle is driving on a highway with a vehicle ahead. In this case, the first VACP calculator 11 uniformly calculates the first VACP value $W_e$ to be 25 by associating the driving actions of a driver typically determined from such a driving environment with the VACP value related to the driving operations of the vehicle.

On the other hand, the SE calculator 12 calculates the SE value $ep_1$ of the driver based on information related to the steering angle acquired by the driving environment recognition unit 20.

Based on the general relational expression $f(ep_g)$ between the SE and VACP of a general driver and the individual relational expression $g(ep)$ between the SE and VACP of an individual, the correction value calculator 13 calculates the general VACP value $f(ep_1)$ and the individual VACP value $g(ep_1)$ corresponding to the SE value $ep_1$ calculated by the SE calculator 12. For example, the correction value calculator 13 calculates the general VACP value $f(ep_1)$ to be 25 and the individual VACP value $g(ep_1)$ to be 40.

Accordingly, the correction value calculator 13 calculates the ratio of the individual VACP value $g(ep_1)$ to the general VACP value $f(ep_1)$ to be 40/25.

The driving load estimation apparatus 10 multiplies the VACP correction value $a_i$ of 40/25, calculated by the correction value calculator 13, by the first VACP value $W_e$ of 25. The driving load estimation apparatus 10 thus calculates that in the driving environment of driving on a highway with a vehicle ahead, the corrected first VACP value $W_i'$ of the individual driver is 25×(40/25)=40.

Figure 4:
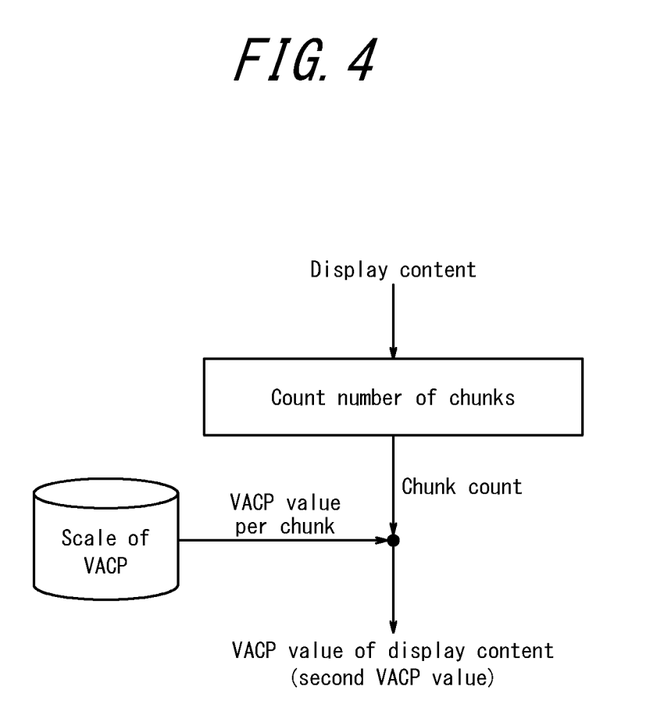
FIG. 4 is an example flowchart for the driving load estimation apparatus to calculate the VACP value based on the information amount of display content.

FIG. 4 is an example flowchart for the driving load estimation apparatus 10 to calculate the VACP value based on the information amount of display content.

The second VACP calculator 14 calculates the chunk count of the display content displayed on the display 40. The second VACP calculator 14 also calculates the VACP value per chunk, for example, based on the VACP scale in Table 1. The second VACP calculator 14 calculates the second VACP value $W_c$ of the display content by multiplying the calculated chunk count of the display content by the VACP value per chunk.

The second VACP calculator 14 is not limited to this method of calculating the second VACP value $W_c$ and may calculate the second VACP value $W_c$ by any optimal method. For example, the second VACP calculator 14 may associate a second VACP value $W_c$ with the display content having the smallest chunk count among a plurality of display contents and calculate the second VACP value $W_c$ of the other display contents based on the ratio of the chunk counts, as described below with reference to FIG. 5.

Figure 5:
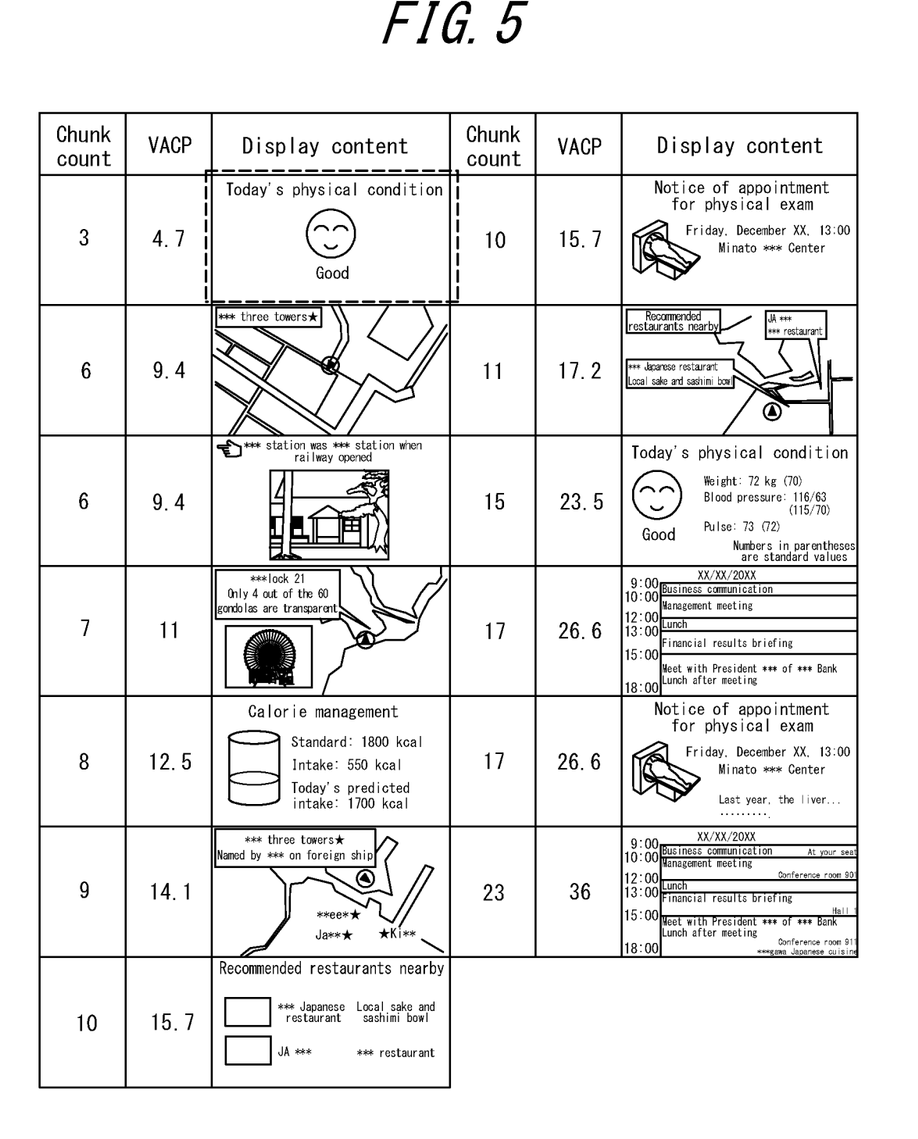
FIG. 5 schematically illustrates an example of how display content and chunk count are related to the VACP value.

FIG. 5 schematically illustrates an example of how display content and chunk count are related to the VACP value.

The second VACP calculator 14 calculates the chunk count of the display content surrounded by dashes in FIG. 5 as 3, for example. The second VACP calculator 14 calculates the second of the VACP value $W_c$ of the display content as 4.7 by adding the scores of "Visually register/detect image" (1.0) under "Visual (V)" and "Sign/signal recognition" (1.0) under "Cognitive (C)" (3.7) in the VACP scale in Table 1. The second VACP calculator 14 calculates the second VACP value $W_c$ of another display content by taking this second VACP value $W_c$ (4.7) as a standard and multiplying it by the ratio of the chunk count of the other display content to the chunk count of the above display content (3). For example, the second VACP value $W_c$ of the display content with a chunk count of 6 is calculated as 4.7×(6/3)=9.4.

The driving load estimation apparatus 10 as described above can estimate a subjective driving load for each driver as an objective numerical value by applying the VACP scale to driving load estimation.

The driving load estimation apparatus 10 can estimate the driving load for each individual in accordance with the driving environment by correcting the first VACP value $W_e$ using the VACP correction value $a_i$. The driving load estimation apparatus 10 can estimate the driving load for each driver taking into account individual differences in the driving load stemming from the driver's degree of experience or the like. The driving load estimation apparatus 10 can thereby appropriately estimate the driving load for the driver and the driving environment. The information control system 1 can therefore provide display information to the driver in an optimal form. The driving load estimation apparatus 10 can perform objective evaluation in accordance with circumstances by correcting the VACP value based on parameters acquirable in real time while the vehicle is driven. The driving load estimation apparatus 10 can estimate the driving load in real time.

The driving load estimation apparatus 10 can more faithfully quantify the steering state in the driving environment by calculating the SE value of the driver based on information related to the steering angle. The driving load estimation apparatus 10 can thereby quantify the subjective load state of each driver as the SE value, which is an objective numerical value.

The driving load estimation apparatus 10 can quantify the individual difference from a general driver as a correction value by deriving the VACP value of a general driver and of each driver in correspondence with the SE value and then calculating the ratio between the VACP values. The driving load estimation apparatus 10 can calculate a better average of the VACP value of the driver by statistically obtaining correlation data of general drivers in advance for a plurality of drivers. The driving load estimation apparatus 10 can thereby accurately calculate the VACP value of a general driver as the standard for the correction value. By accumulating correlation data for each driver, the driving load estimation apparatus 10 is able to calculate better correction values for individuals.

The driving load estimation apparatus 10 multiplies the VACP correction value $a_i$ by the first VACP value $W_e$ and can thereby accurately reflect the individual difference between a general driver and each driver and correct the first VACP value $W_e$ uniformly based on the driving environment.

The driving load estimation apparatus 10 calculates the second VACP value $W_c$ based on the information amount of the display content and can thereby quantify the load due to the information amount of the display content using the same scale as for the driving load based on driving actions. The driving load estimation apparatus 10 can easily compare these two loads as numerical values quantified on the same scale.

The driving load estimation apparatus 10 can measure the information amount of the display content more objectively by defining the information amount according to the chunk count. The driving load estimation apparatus 10 can accurately quantify the information amount of the display content as a VACP value by calculating the second VACP value $W_c$ to correspond to the chunk count.

The driving load estimation apparatus 10 can collectively estimate the load due to the driving actions and the information amount of the display content by adding the second VACP value $W_c$ to the corrected first VACP value $W_i'$. The driving load estimation apparatus 10 can thereby contribute to optimal information control by the information control system 1 for each driver.

The information control system 1 can perform better information control for individual drivers by using the driver capacity calculator 31 to calculate the capacity of the driver for the driving load.

Although the present disclosure has been explained with reference to the drawings and examples, it is to be noted that various changes and modifications will be apparent to those of ordinary skill in the art based on the present disclosure. Therefore, such changes and modifications are to be understood as included within the scope of the present disclosure. For example, the functions and the like included in the various means, steps, and the like may be reordered in any logically consistent way. Furthermore, means, steps, or the like may be combined into one or divided.

For example, the driving load estimation apparatus 10 is not limited to calculating the SE value of the driver based on a steering operation. Any configuration that can objectively quantify a steering operation by an individual driver may be adopted.

The driving load estimation apparatus 10 is not limited to calculating the ratio of the individual VACP value $g(ep_1)$ to the general VACP value $f(ep_1)$. Any configuration that can appropriately obtain the VACP correction value $a_i$, may be adopted. For example, instead of using correlation data of a general driver, the driving load estimation apparatus 10 may use correlation data between the first VACP value $W_e$ and the SE value determined uniformly based on information related to the driving environment. The correlation data between the first VACP value $W_e$ and the SE value is stored in advance in any recording medium as a database. In this case, the driving load estimation apparatus 10 may acquire the VACP correction value $a_i$ by comparing the SE value corresponding to the first VACP value $W_e$ calculated by the first VACP calculator 11 with the SE value calculated in real time by the SE calculator 12 to determine the ratio thereof.

The driving load estimation apparatus 10 is not limited to performing correction by multiplying the VACP correction value $a_i$ by the first VACP value $W_c$ and may instead perform correction by any calculation method allowing the first VACP value $W_c$ to be corrected appropriately.

The driving load estimation apparatus 10 is not limited to determining the information amount of the display content by the chunk count and may adopt any method that can objectively quantify the information amount.

The driving load estimation apparatus 10 is not limited to adding the second VACP value $W_c$ to the corrected first VACP value $W_i'$ and may adopt any suitable configuration that can collectively quantify the load of the driver.

REFERENCE SIGNS LIST

1 Information control system
10 Driving load estimation apparatus
11 First VACP calculator
12 SE calculator
13 Correction value calculator
14 Second VACP calculator
20 Driving environment recognition unit
30 Controller
31 Driver capacity calculator
32 Display information control unit
40 Display 41 HUD
42 Meter display
43 Center display

The invention claimed is:

1. A driving load estimation apparatus comprising:
a driving environment recognition unit including:
a plurality of sensors configured to collect environment information, the plurality of sensors including a steering angle sensor configured to collect steering angle data; and
a display configured to display content to a driver;
a first VACP calculator configured to calculate a first VACP value based on the environment information collected by the driving environment recognition unit;
a steering entropy calculator configured to calculate a steering entropy value of the driver based on information collected by the steering angle sensor during vehicle operation; and
a correction value calculator configured to calculate a VACP correction value of the driver based on the steering entropy value of the driver;
wherein the driving load estimation apparatus is configured to estimate a driving load of the driver by correcting the first VACP value based on the VACP correction value and display the content on the display to edit an amount of information received by the driver based upon the driving load of the driver; and
wherein the correction value calculator is configured to:
calculate an individual VACP value, based on the steering entropy value of the driver, as a VACP value of the driver used for a steering operation in a driving environment;
calculate a general VACP value, based on the steering entropy value of the driver and a general relational expression indicating a relationship between the steering entropy value and a VACP value of a general driver, as a VACP value of a general driver for a steering operation in the driving environment; and
acquire the VACP correction value based on the general VACP value and the individual VACP value.

2. The driving load estimation apparatus of claim 1, wherein the correction value calculator is configured to calculate a ratio of the individual VACP value to the general VACP value to acquire the VACP correction value.

3. The driving load estimation apparatus of claim 1, wherein the correction value calculator is configured to calculate the individual VACP value based on the steering entropy value of the driver and an individual relational expression indicating a relationship between the steering entropy value and the individual VACP value.

4. The driving load estimation apparatus of claim 1, wherein the driving load estimation apparatus is configured to correct the first VACP value by multiplying the VACP correction value by the first VACP value.

5. The driving load estimation apparatus of claim 1, further comprising a second VACP calculator configured to calculate a second VACP value based on an information amount of display content.

6. The driving load estimation apparatus of claim 5,
wherein the information amount of the display content is determined by a chunk count defined by a character count, a word count, a count of phrases, icons, and figures, or a count of attention points in graphic form; and
wherein the second VACP calculator is configured to calculate the second VACP value to correspond to the chunk count.

7. The driving load estimation apparatus of claim 5, wherein the driving load estimation apparatus is configured to add the second VACP value to a corrected first VACP value.

8. The driving load estimation apparatus of claim 1, wherein the general relational expression is set based on correlation data between the steering entropy value and the VACP value of the general driver, the correlation data being calculated statistically in advance for a plurality of drivers.

\* \* \* \* \*